(12) United States Patent
McNally

(10) Patent No.: US 6,365,343 B1
(45) Date of Patent: Apr. 2, 2002

(54) INTERCELLULAR ADHESION MOLECULE POWDER FORMULATION

(75) Inventor: Eugene J. McNally, Southbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/117,087
(22) PCT Filed: Mar. 4, 1997
(86) PCT No.: PCT/US97/03263
§ 371 Date: Jul. 28, 2000
§ 102(e) Date: Jul. 28, 2000
(87) PCT Pub. No.: WO97/32596
PCT Pub. Date: Sep. 12, 1997

Related U.S. Application Data
(60) Provisional application No. 60/012,944, filed on Mar. 6, 1996.

(51) Int. Cl.[7] .................................................. C12Q 1/70
(52) U.S. Cl. ...................... 435/5; 435/343.1; 435/343.2
(58) Field of Search ............................ 530/300, 388.75, 530/389.2; 435/343.2, 5, 343.1; 424/43

(56) References Cited

U.S. PATENT DOCUMENTS 5,235,049 A * 8/1993 McClelland et al. ...... 435/240.2
5,859,212 A * 1/1999 McClelland et al. ........ 530/413

FOREIGN PATENT DOCUMENTS

WO    WO 96/40069    12/1996

OTHER PUBLICATIONS

Ahn et al. Journal of Microencapsulation, vol. 12 (4), pp. 363–375 (abstract only), Jul. 1995.*
Wong et al. Antimicrobial Agents and Chemotherapy, vol. 39, No. 11, pp. 2574–2576 Nov. 1995.*
Marlin et al . Nature, vol. 344, pp. 70–72 Mar. 1990.*

* cited by examiner

Primary Examiner—Ali R. Salimi
(74) Attorney, Agent, or Firm—R. P. Raymond; M-E. M. Devlin

(57) ABSTRACT

The present application discloses a finely divided, dry powdered pharmaceutical composition which is specially adapted to be administered as an insufflate which includes the following ingredients:

(a) an pharmacologically effective amount of sICAM-1;
(b) an amount of carboxymethyl cellulose which is effective to retain sICAM-1 on the intranasal membranes;
(c) an amount of a bulking agent which is effective to provide a bulking effect without exerting a significant effect on the retention of the sICAM-1 on the nasal passages.

3 Claims, No Drawings

INTERCELLULAR ADHESION MOLECULE POWDER FORMULATION

RELATED APPLICATIONS

This application claims benefit of Provisional Application Ser. No. 60/012,944, filed Mar. 6, 1996 and PCT International Application PCT/US97/03,263, filed Mar. 4, 1997.

TECHNICAL FIELD

The present invention provides a novel composition for nasal insufflation which provides a means for the administration of the extracellular portion of the Intercellular Adhesion Molecule (sICAM-1).

BACKGROUND ART

The sICAM-1 molecule and its antiviral effects are disclosed in EPA 391088-A and U.S. Application Ser. No. 08/479,557, filed Jun. 7, 1995 which are incorporated by reference. ICAM-1 is disclosed in U.S. 5,284,931, which is incorporated by reference. This drug is active as a competitive antagonist for rhinovirus binding. The intranasal administration of sICAM-1 is mentioned in Ser. No. 07/514,033 but the concept of formulating sICAM-1 as an insufflate for nasal administration is not disclosed. Various diluents are mentioned for use in preparing controlled release pharmaceutical compositions of sICAM-1 including carboxymethylcellulose but there is no disclosure of the use of any concentration of carboxymethylcellulose sodium salt or of the concept of formulating a long acting nasal insufflate.

The normal nasal residence time for most drugs that are placed in the nasal passages is from 15 to 20 minutes. The residue of any drug that is not systemically absorbed through the nasal membranes is cleared to the posterior portion of the nasopharynx and swallowed by the patient. The relatively large molecular weight of sICAM-1 (82,000 daltons) prevents the systemic absorption of any substantial amount of the drug from the nasal passages.

Insufflates are generally recognized as finely divided powders that are directly introduced into a body cavity by means of an insufflator or powder blower to achieve a local or systemic effect. Insufflates may also be administered from a pressurized aerosol which provides accurate control of the dose which is administered by using a metered aerosol valve. In order to administer, by insufflation, a drug which is intended to have a local effect in the nasopharynx, it is necessary to formulate the drug in a solid diluent which is pharmaceutically acceptable and does not interfere with the dispersion of the drug, does not interfere with the adhesion of the drug to the mucus membranes, does not have an adverse effect on the shelf life of the drug and is not excessively hygroscopic so that it may cause the formation of large particles in the composition during storage under ambient conditions. For these reasons it is desirable to provide a stable sICAM-1 therapeutic composition which will enhance the retention of the protein in the nasal passages.

DISCLOSURE OF THE INVENTION

The applicant has discovered a novel composition for the intranasal administration of sICAM-1 which is based on the use of a carrier system which comprises carboxymethylcellulose sodium as a solid diluent for the sICAM-1.

Accordingly, it is a primary object of this invention to provide a dry composition of sICAM-1 which is suitable for administration by insufflation.

It is also an object of this invention to provide a dry composition of sICAM-1 which does not interfere with the dispersion of the drug.

It is also an object of the invention to provide a dry composition of sICAM-1 which promotes the adhesion of the drug to the mucus membranes.

It is also an object of the invention to provide a dry composition of sICAM-1 which does not have an adverse effect on the shelf life of the drug.

It is also an object of the invention to provide a dry composition of sICAM-1 which is not excessively hygroscopic so that it may cause the formation of agglomerates in the composition during storage under ambient conditions.

It is also an object of the invention to provide a dry composition of sICAM-1 which is compatible with a hard gelatin capsule.

These and other objects of the invention will become apparent from a review of the appended specification.

MODES FOR CARRYING OUT THE INVENTION

The invention provides a finely divided, dry powdered pharmaceutical composition adapted to be administered as an insufflate, said dry powdered pharmaceutical composition comprising:

(a) an therapeutically effective amount of sICAM-1;
(b) an amount of carboxymethyl cellulose which is effective to retain sICAM-1 on the intranasal membranes;
(c) an amount of a bulking agent to produce a pharmaceutically elegant product which is effective to prevent the collapse of the carboxymethylcellulose and the sICAM-1 during lyophylization.

The formulation will be prepared to provide a delivered dose of from 0.1 to 1.0 mg and preferably from 0.05 to 75 mg of sICAM-1 to the intranasal passages by the introduction of one single inhalation of the insufflate.

sICAM-1 is a genetically engineered form of the extracellular portion of the sICAM-1 receptor and as such acts as a competitive antagonist for rhinovirus binding to host cells. This material is also known as BIRR 4 and is a single chain recombinant, soluble glycoprotein derived by genetic engineering from a naturally occurring transmembrane glycoprotein sICAM-1. BIRR 4 is a truncated form of the intercellular adhesion molecule 1(ICAM-1) containing the amino acids that comprise the extracellular domain of the molecule. Based on DNA, sequence analysis, BIRR 4 is predicted to contain five immunoglobulin-like domains stabilized by intrachain disulfide bonds.

The premise in using sICAM-1 in the prevention and/or early treatment of the common cold is based on the fact that the sICAM-1 compound will prevent the rhinovirus from becoming attached to the mucous membrane of the nose. In order to protect the nasal membranes from the rhinovirus, it is desirable to substantially completely contact the nasal mucous membranes with the sICAM-1 molecule in order that the sICAM-1 molecule will be distributed across the mucous membrane surface where it will interact with any rhinovirus particles that may be present in the nasal passages and prevent or attenuate the clinical progress of any infection. The intended hosts for treatment with the product of the invention include primates such as humans who may be treated to relieve the symptoms of a rhinovirus infection or for the prophylaxis of a rhinovirus infection.

The applicants have discovered that the use of carboxymethylcellulose sodium as a carrier for sICAM-1 provides an insufflate which extends the action of sICAM-1 in the nasal passages as compared to compositions which are based on aqueous solutions of sICAM-1 or which are insufflates of sICAM-1 that are based on the use of hydroxypropyl cellulose or hydroxyethylcellulose. In addition, the applicant has discovered that the addition of a bulking agent which may be a sugar alcohol such as sorbitol, mannitol or galactitol, or an amino acid such as glycine or a polymer such as a carbohydrate based polymer which may be dextran or cyclodextrin to the sICAM-1 combination with carboxymethylcellulose sodium will provide a bulking effect without exerting a significant effect on the retention of the sICAM-1 on the nasal passages.

The particular carboxymethyl cellulose sodium used in the invention will be a pharmaceutical grade that will have a minimum purity of 99.5%. Generally the preferred carboxymethyl cellulose sodium will have a viscosity in water of 150 to 250 cps when measured at a temperature of 25° C. and a concentration of 1 wt %. If desired, carboxy methylcelluloses having different molecular weights may be blended together to obtain a product having a desired viscosity.

The composition of the invention will also include inorganic salts which will provide a buffered pH of about 6.0. Generally, an alkali metal chloride such as sodium or potassium chloride is combined with sodium monobasic phosphate and the pH is adjusted with an alkali metal hydroxide such as sodium hydroxide or potassium hydroxide.

The insufflate is preferably made by dissolving the components in water and removing the water by lyophilization and passing the product of lyophilization through an appropriately sized sieve to provide a free flowing powder which is finely divided and suitable for administration using a suitable inhaler.

The method in which the powder components are combined to form the lyophillizable composition is important because if the powders are not combined according to the following procedure, the biological activity of the sICAM-1 may be adversely affected. It is preferred to prepare a solution of the sICAM-1 in the phosphate buffer by dialyzing the sICAM-1 from the solution in which sICAM is produced into the phosphate buffer solution using a polysulfone diafiltration membrane. A solution of the carboxy methyicellulose sodium and the bulking agent are separately prepared by dry blending the powdered components prior to dispersing the mixed components in water at 45 to 55° C. and preferably at about 50° C. The dry blending of the bulking agent and the carboxymethyl cellulose sodium facilitates the wetting of the carboxymethyl cellulose sodium and minimizes the aggregation of the polymer when it is dispersed in water. After the powders are combined with water, it is preferred to employ a high shear mixing apparatus such as a Waring blender for 2 to 10 minutes to disperse the, powders in the water. The dispersed mixture is then filtered through an appropriate filter e.g 5 to 50 microns, and allowed to cool to room temperature.

After the polymer has cooled to room temperature, equal weights of the polymer solution and the sICAM-1 solution are mixed and placed in lyophilization vials. The vials are loaded into a lyophilizer and freeze dried.

Generally the compositions which are prepared for lyophilization will contain:

| | Concentration wt % |
|---|---|
| sICAM-1 | 0.1 to 1% |
| Bulking agent | 2 to 10% |
| Carboxymethyl cellulose, Na | 1 to 3% |
| Alkali metal chloride | 0.1 to 0.6.% |
| Sodium Phosphate, monobasic | 0.1 to 0.6% |
| Sodium hydroxide | qs. to pH 6.0 |
| Water | qs* |

*sufficient to prepare aqueous solution (removed by lyophilization)

The dry powdered pharmaceutical composition will include in weight %:

| sICAM-1 | 0.07 to 7% |
|---|---|
| Bulking agent | 70 to 90% |
| Carboxymethyl cellulose, Na | 14 to 45%. |

The preferred dry powdered pharmaceutical composition will include in weight %:

| sICAM-1 | 1 to 5% |
|---|---|
| Bulking agent | 80 to 90% |
| Carboxymethyl cellulose, Na | 14 to 21%. |

Generally it will be preferred to package a single therapeutic dose of the powder in two piece hard gelatin capsules which may be opened just prior to use. Each capsule may contain from 5 to 20 mg of composition with from 0.01 to 1.0 mg of sICAM-1. The powder is placed directly in an inhaler or the intact capsule may be placed in an inhaler which is adapted to open the capsule and to expel the powder contents of the capsule in a form where it is mixed with air and may be directly inspired into the patient's nose.

For use in this type of an inhaler, the gelatin capsule should have hemispherical ends which interact with the inhaler to provide for proper dispensing of the powder. An example of a useful apparatus for the practice of the invention is described in U.S. Pat. No. 4,889,114, which is incorporated by reference. That apparatus may be provided with a nasal tip such as a DeVilbiss nasal tip, Model 40-TR, The following example is added to illustrate a preferred embodiment of the invention and is not intended as a limiting description of the invention.

EXAMPLE

The preparation of ICAM-1 is described in U.S. Pat. No. 5,284,931. In order to produce a truncated soluble derivative of ICAM-1 which lacks the cytoplasmic domain, an in-frame stop codon (between the Dcyt and D5) is generated using oligonucleotide mutagenesis based on the method of Kunkel, Proc. Natl. Acad. Sci USA 82:488–492 (1985), as modified by Peterson et al. Cell 53:65–72 (1988) both of which are incorporated by reference. The oligonucleotide mutagenesis results in the formation of a mutant ICAM-1 gene, designated Y452 E/F TAG, which, upon expression results in the formation of a truncated, secreted form of ICAM-1 (sICAM-1).

An expression vector consisting of the hamster DHFR gene and the coding region of the above described mutant ICAM-1 controlled by the promoter, splice signals and polyadenylation signal from the SV40 early region was constructed. The hamster DHFR gene was isolated for the plasmid pBR322DHFR (Mulligan, R. et al., Proc. Natl. Acad. Sci. USA 78:2072–20766 (1981) by digestion with FspI and HindIII, followed by blunt end ligation into pSV2gpt (Mitchell et al, Mol. Cell. Biol. 6:425–4490 (1986) cleaved with BamHI/HindIII. The mutant sICAM-1 (soluble ICAM-1) cDNA was isolated by digestion with NotI. The ends were then filled in using Klenow, and the molecules were then digested with HindIII. The molecules were then ligated with pBR322DHFR expression vector (prepared by digestion with ApaI, ends then filled with Klenow, and digested with HindIII to remove the gpt gene). Thus, the sICAM-1 gene was physically linked to the hamster gene in a SV40 expression vector.

The completed vector was then transfected into Chinese hamster ovary (CHO) K1 DUX-B11 cells using the calcium phosphate coprecipitation method (Graham et al. Virology, 52:456–467 (1973). After two days of growth in nonselective mediur, the cells were passaged in selective medium containing 0.05 to 2 $\mu$M of methotrexate, but lacking hypoxanthine and thymidine. Clones were isolated, subcloned, and tested for sICAM-1 production by Elisa. Colonies secreting the greatest quantity of sICAM-1 were then subjected to two further rounds of gene amplification, and a stable cell line, designated CHO118A, was derived. This cell line which is a preferred source of sICAM-1, secreted sICAM-1 into the culture supernate to approximately 1 $\mu$g/ml.

The sICAM-1 was purified from supernates of CHO118A cells by immunoaffinity chromatography with anti-ICAM-1 monoclonal antibody R6.5. For this purpose R6.5 was covalently coupled, to CNBr-activated Sepharose 4B (Pharmacia LkB) to a final concentration of 5 mg per ml of packed resin according to the manufacturers instructions. All chromatographic steps were done at 4° C., and all buffers contained 0.2 U/ml aprotinin and 1 mM of phenylmethyl-sulfonyl fluoride. One liter of filtered supernate containing approximately 1 mg of sICAM-1 was loaded into a column of R6.5 Sepharose at a flow rate of 1 ml/minute. The column was then washed with 200 ml of 10 mM Tris/0.15 M NaCl at a flow rate of 2.5 ml/minute to remove unbound material. The bound sICAM-1 was eluted with 50 mM triethylamine/0.15 M NaCl/pH 11.0 at a flow rate of 1 ml/minute. Fractions were collected and immediately neutralized by the addition of 1M Tris, pH 6.0 to a final concentration of 20 mM.

Fractions containing the eluted sICAM-1 were identified by SDS-PAGE on 10–15% polyacrylamide gradient gels followed by silver staining. Electrophoresis and staining were done using a Pharmacia Phastgel system and silver staining kit according the manufacturers instructions. The fractions containing sICAM were pooled and concentrated approximately 10 fold using Centricon-30 microconcentrators (Amicon, Danvers, Mass.).

The protein content of one batch of purified sICAM-1 was determined using a Bio-Rad Protein Assay according to the manufacturer's instructions (Bio-Rad Laboratories, Richmond, Calif.) and this material was frozen in aliquots for use as reference standards. Subsequently, the concentration of sICAM-1 in samples was determined in a "sandwich" type ELISA using those reference standards and two anti-ICAM-1 monoclonal antibodies, R6.5 and R6.1 (Rothlein et al. J. Immunol. 141:1665–1669 (1988), that bind to non-overlapping epitopes. R6.1 was bound to the plastic in 96 well plates by incubating 10 $\mu$l of a 10 $\mu$g/ml solution for 1 hour at 37° C. Each of the following steps was then done with 100 $\mu$l of reagent incubated at 37° C. for 20 minutes, followed by washes with phosphate buffered saline: (1) binding of serial dilutions of reference standard sICAM-1 or unknowns; (2) binding of biotinylated R6.5 (1 $\mu$g/ml); and (3) binding of horseradish peroxidase-conjugated streptavidin (Zymed Laboratories, South San Francisco, Calif.) at the manufacturers recommended concentration. After the addition of the substrate ABTS (Zymed), and incubation for 20 minutes at room temperature, the absorbance was determined at 410 nm in a spectrophotometer. The concentration was determined by comparison to a reference standard curve.

sICAM-1 is dialyzed against a phosphate buffer using a polysulfone membrane to provide a solution of sICAM-1 which contains a concentration of 10 mg of sICAM-1; 3.4 mg sodium phosphate and 3.6 mg sodium chloride/ 1 ml of solution.

Carboxymethylcellulose (CMC) (20 g) and mannitol (100 g) are dry blended together. Water (750 ml) preheated to 50° C. is agitated in a Waring blender set at low speed, and the dry blend of the CMC and the mannitol is added to the perimeter of the vortex in the Waring blender. As the viscosity increases, slowly increase the blender speed while continuing to add the powder blend. The mixture should be added over the course of approximately two minutes. When the powder addition is complete, the volume of solution should be brought to one liter with the addition of 50° C. water and mixing continued for 5 minutes. The warm mixture is filtered through a 10 micron filter and allowed to cool to room temperature. Once the polymer solution is cooled to room temperature, equal weights of the carboxymethyl cellulose sodiummannitol solution are mixed with the sICAM-1 solution and 1 g of solution is placed in 5 ml lyophilization vials. The vials are loaded into a lyophilizer and freeze dried according to the following schedule:

step 1: product is placed on the lyophilizer shelf and the condenser is set to –50° C.;

step 2: when the condenser reaches –50° C., the vacuum is started and maintained at 100 millitorr;

step 3: when the product temperature reaches –50° C., the shelf temperature is raised to –28° C. at a rate of 0.5° C./minute;

step 4: hold the temperature at –28° C. for 15 hours;

step 5: raise temperature to 25° C. at a rate of 0.5° C./minute;

step 6: hold temperature at 25° C. for 3.5 hours;

step 7: lower temperature to 4° C. at 0.5 °/minute step 8: hold temperature at 4° C. until vials are stoppered under vacuum; and step 9: remove product from lyophilizer.

The product from step 9 is sequentially passed through two US standard sieves (#18 and #35) to obtain a fine even powder. Thereafter 15 mg of the product is placed in a No. 3 two piece hard gelatin capsule.

The efficacy of the product was demonstrated in an animal model using young farm pigs. To visualize the intranasal retention of the product, sICAM-1 was radiolabled with $^{123}$I using a commercially available iodination kit (Iodobeads, Pierce) and then incorporated into the CMC formulation and the control compositions listed below. Control compositions using a phosphate buffered saline solution having the formula: 50 mM monobasic phosphate, 104 mM sodium chloride, pH 6; a hydroxy propyl cellulose (HPC) power based composition having the formula: 1% wv HPC, 5% wv Mannitol; and a hydroxy ethyl cellulose (HEC) powder based composition have the formula: 1% wv HEC, 5% wv Mannitol were prepared in an analogous manner as previously described for the CMC formulation. For the powder CMC and control compositions, the lyophilized materials were reduced in particle size to a fine powder using a metal spatula and 30–50 mg of powder was filled into a 1 ml plastic disposable pipette tip. The pipette tip, attached to a hand held pipette bulb, was inserted 1–1.5 cm into each nostril and the bulb was squeezed to provide sufficient pressure to deliver the powders into the animals nose. The phosphate buffered saline solution formulation was administered in a similar manner in 0.1 ml aliquots. All of these clearance studies used approximately 20–50 microcuries of $^{123}$I sICAM-1 tracer. Following dosing, the animal was placed in front of an external gamma scintigraphy camera and data was collected for 90 minutes. Raw count data were corrected for decay and then converted to percent retention which was normalized to the initial deposited dose of $^{123}$I sICAM-1. The results were as follows:

| COMPOSITION | PERCENT OF DOSE RETAINED 90 MINUTES AFTER ADMINISTRATION |
| --- | --- |
| Solution formulation | 30% |
| Carboxymethyl cellulose sodium | 80% |
| Hydroxypropyl cellulose | 50% |
| Hydroxyethyl cellulose | 60% |

These tests show that the retention time on the nasal membrane, for the composition of the invention, is surprising and unexpected.

The invention has been described in connection with the specific embodiments thereof and it will be understood that it may be modified and that this application is intended to cover any variations, uses or adaptations of the invention following, in general, the principles of the invention and including such departures from the present disclosure as come within known or customary practice within the art to which the invention pertains and as may be applied to the essential features hereinbefore set forth in the appended claims.

What is claimed is:

1. A method of treating rhinovirus infection in a warm-blooded animal comprising using an insufflate for nasal administration and wherein the drug in such insufflate is soluble intercellular adhesion molecule, type I (sICAM-1), the improvement which comprises using as the insufflate a dry, powdered pharmaceutical composition comprising:

(a) sICAM-1 is an amount of about 0.07 to about 7% by weight;
    (b) a bulking agent selected from the group consisting of amino acids, sugar alcohols and carbohydrate based polymers, in an amount of about 70% to about 90% by weight; and
    (c) carboxymethyl cellulose, Na, in an amount of about 14% to about 45% by weight, where the dry, powdered pharmaceutical composition is sequentially passed through U.S. standard sieves #18 and #35.

2. The method as recited in claim 1 wherein the bulking agent in the dry, powdered pharmaceutical composition is a sugar alcohol selected from the group consisting of sorbitol, mannitol and galactitol.

3. The method as recited in claim 1 wherein the dry, powdered pharmaceutical composition further comprises a phosphate buffer.

* * * * *